United States Patent [19]
Mick et al.

[11] Patent Number: 5,860,909
[45] Date of Patent: Jan. 19, 1999

[54] SEED APPLICATOR FOR USE IN RADIATION THERAPY

[75] Inventors: Felix W. Mick, Bronxville; Kenneth Zabrouski, Bethpage, both of N.Y.

[73] Assignee: Mick Radio Nuclear Instruments, Inc., Bronx, N.Y.

[21] Appl. No.: 733,842

[22] Filed: Oct. 18, 1996

[51] Int. Cl.$^6$ .............................. A61N 5/00; A61M 31/00
[52] U.S. Cl. ................................................................ 600/7
[58] Field of Search ........................ 600/1–8; 604/37–64, 604/93

[56] References Cited

PUBLICATIONS

Mick 200–TP Applicator Instruction Manual, Catalog #8810, Mar. 1995.
Brachytherapy Interstitial & Intracavitary Applicators & Accessories, Catalog 9301, pp. 1–4, 1993.
Mick Applicator for the Implantation of $^{125}$I Seeds and $^{198}$Au Grains, Catalog #7308. 1973.

*Primary Examiner*—John P. Lacyk
*Assistant Examiner*—Samuel Gilbert
*Attorney, Agent, or Firm*—Kenyon & Kenyon

[57] ABSTRACT

An applicator is disclosed for implanting seeds at variably spaced locations in a patient's body. The applicator includes a needle insertable into the body, a base member adapted to be maintained generally stationary with respect to a surface of the body during use, and a needle chuck, which is slidably mounted with respect to the base member, for releasably coupling the needle. The applicator also includes a seed magazine mounted on the needle chuck for dispensing seeds into the needle bore, a stylet extendable through the needle bore for forcing seeds in the bore into the patient's body, and a barrel attached to the needle chuck. The barrel includes five rows of spaced indentations. The indentations in each row are generally equally spaced from adjacent indentations in that row, and the indentation spacing in each row is different from other rows. A ball plunger, which is movably mounted in the base member, successively engages the indentations of a selected row as the barrel is moved with respect to the base member to releasably fix the needle relative to the base member in a plurality of variably spaced positions relative to the base member in order to enable seeds to be implanted at variably spaced locations in the patient's body.

11 Claims, 5 Drawing Sheets

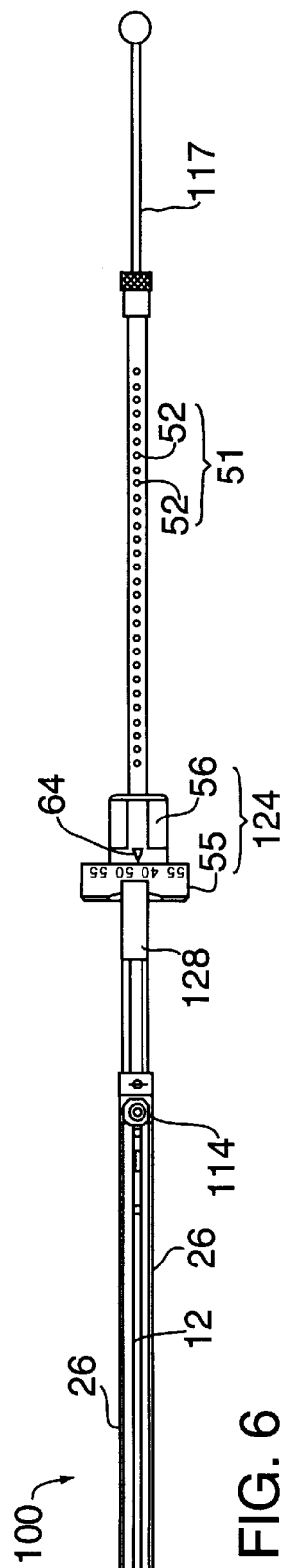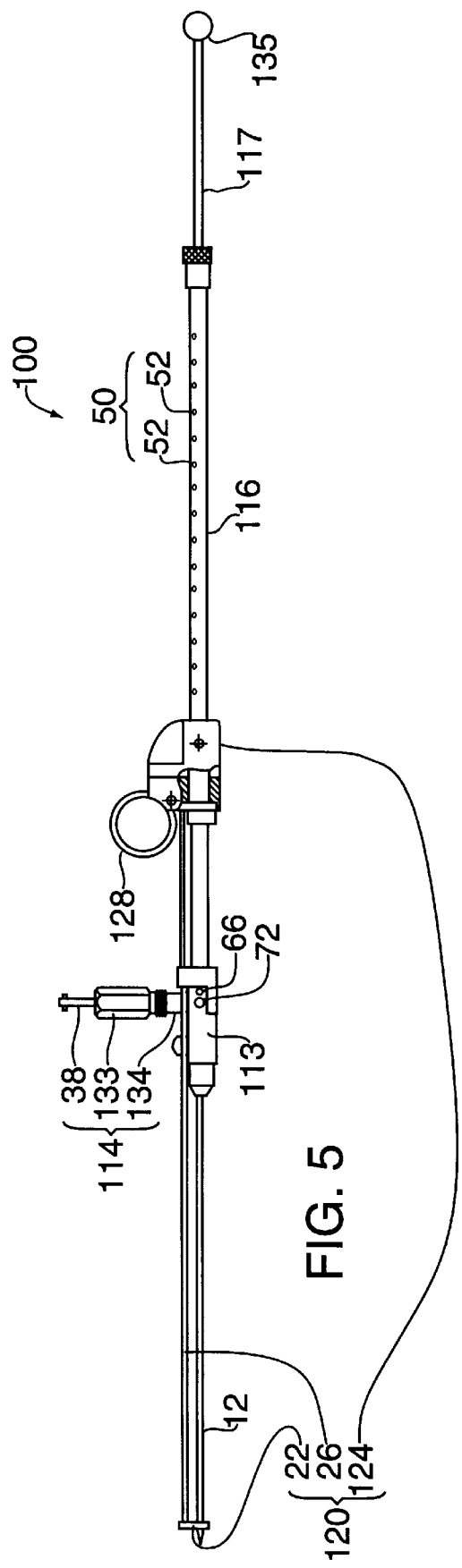
FIG. 6
FIG. 5

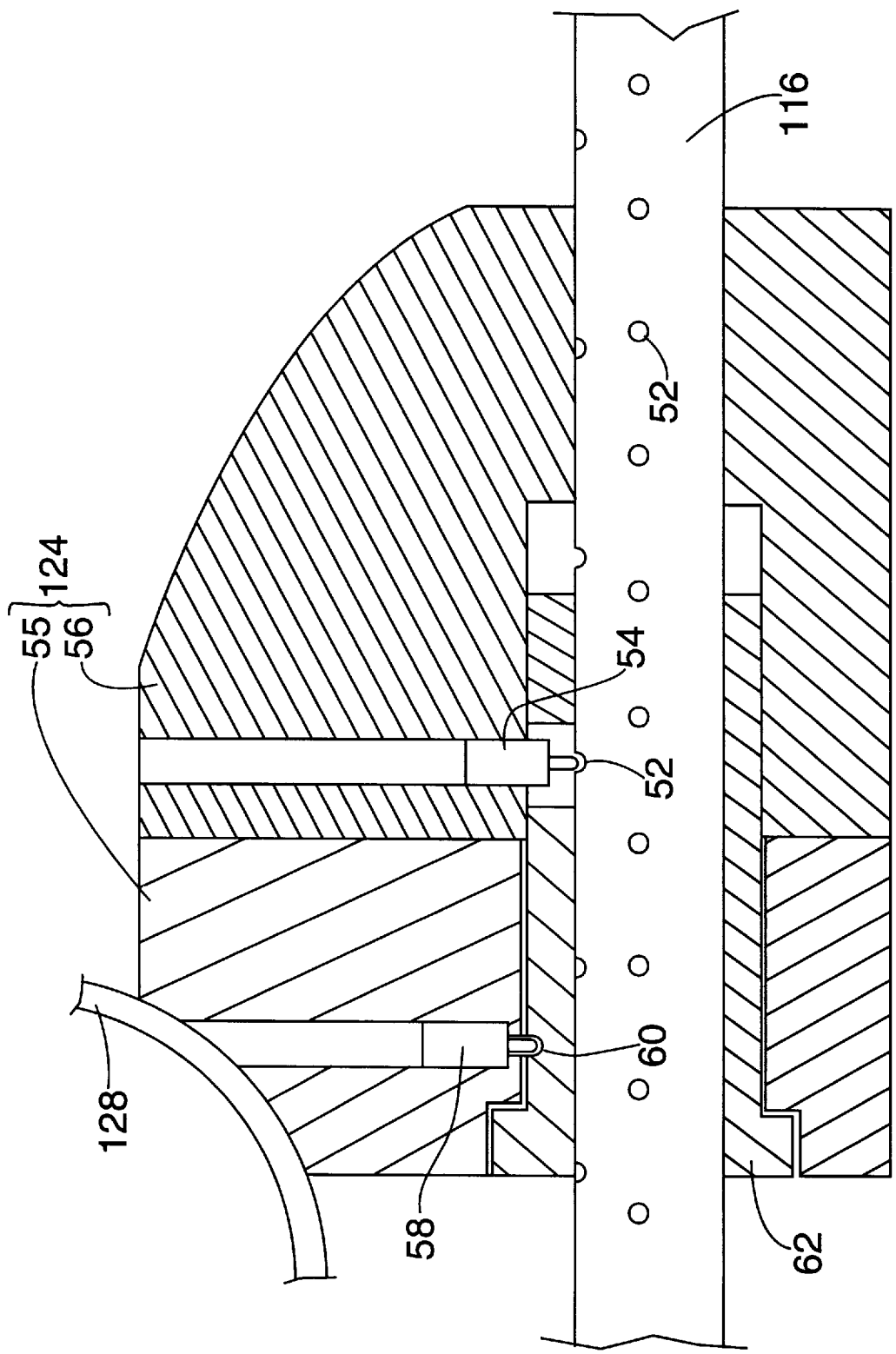

SEED APPLICATOR FOR USE IN RADIATION THERAPY

FIELD OF THE INVENTION

The present invention relates generally to medical instruments and, more particularly, to applicators for implanting radioactive seeds in a patient's body for use in cancer treatment.

BACKGROUND OF THE INVENTION

Cancer treatment often includes implanting radioactive material such as iodine$^{125}$ or palladium$^{103}$ seeds into the area of the patient's body to be treated and thereafter subjecting the body to radiation. A seed applicator is used to implant the seeds at spaced locations in the patient's body.

Prior art seed applicators enable seeds to be implanted at fixed spaced-apart locations in the patient's body. However, it has been found to be clinically advantageous to place seeds in a variety of spacing arrangements not easily possible using the prior art applicators.

Prior art applicators include removable magazines that can be preloaded with seeds. There is a need for a mechanism to ensure that the magazines are properly installed in the applicator. Incorrectly installed magazines have been known to fall out of the applicator during use.

OBJECTS AND SUMMARY OF THE INVENTION

Accordingly, one object of the present invention is to provide a seed applicator that enables seeds to be quickly and easily implanted in a patient's body in a variety of spacing arrangements.

Another object of the invention is to provide a mechanism in the applicator to facilitate proper installation of magazines.

An applicator in accordance with the present invention includes a needle insertable into the body, a base member adapted to be maintained generally stationary with respect to a surface of the body during use, and a needle chuck, which is slidably mounted with respect to the base member, for releasably coupling the needle. The applicator also includes a removable seed magazine, which can be reusable or disposable, mounted on the needle chuck for dispensing seeds into the needle bore. The applicator further includes a barrel attached to the needle chuck and a stylet extendable through the needle bore and barrel for forcing seeds in the needle bore into the patient's body. The barrel includes five rows of spaced indentations extending along the length of the barrel. The indentations in each row are generally equally spaced from adjacent indentations in that row, and the indentation spacing in each row is different from other rows. For example, the applicator may have a first row of indentations spaced at 3.75 mm, a second row of indentations spaced at 4.0 mm, a third row of indentations spaced at 5.0 mm, a fourth row of indentations spaced at 5.5 mm, and a fifth row of indentations at 6.0 mm. These spacings can be changed as desired by using an applicator having a main barrel with other indentation spacings. A ball plunger, which is movably mounted in the base member, successively engages the indentations of a selected row as the barrel is moved with respect to the base member to releasably fix the needle relative to the base member in a plurality of variably spaced positions relative to the base member. This mechanism provides the user with an indication that the needle has been moved a desired distance for spaced seed implants. The row selected for engagement by the ball plunger can be easily changed by turning a spacing dial. The applicator thereby allows seed spacing to be easily and accurately varied as desired.

In accordance with another aspect of the invention, a keying mechanism is provided to ensure that the magazine is properly installed in the applicator chuck. The mechanism permits the magazine to be installed in chuck in only one orientation. Specifically, the chuck includes an index pin and the magazine includes a recess for receiving the index pin to properly orient the magazine during installation and thereby securely retain the magazine in the chuck during use.

BRIEF DESCRIPTION OF THE DRAWINGS

FIG. 5 is a side elevation view of a seed applicator in accordance with the present invention.

FIG. 6 is a top plan view of the FIG. 5 applicator.

FIG. 7 is an enlarged cross-section view of the barrel collar and spacing dial mechanism of the FIG. 5 applicator.

Detailed Description

Figure 1:
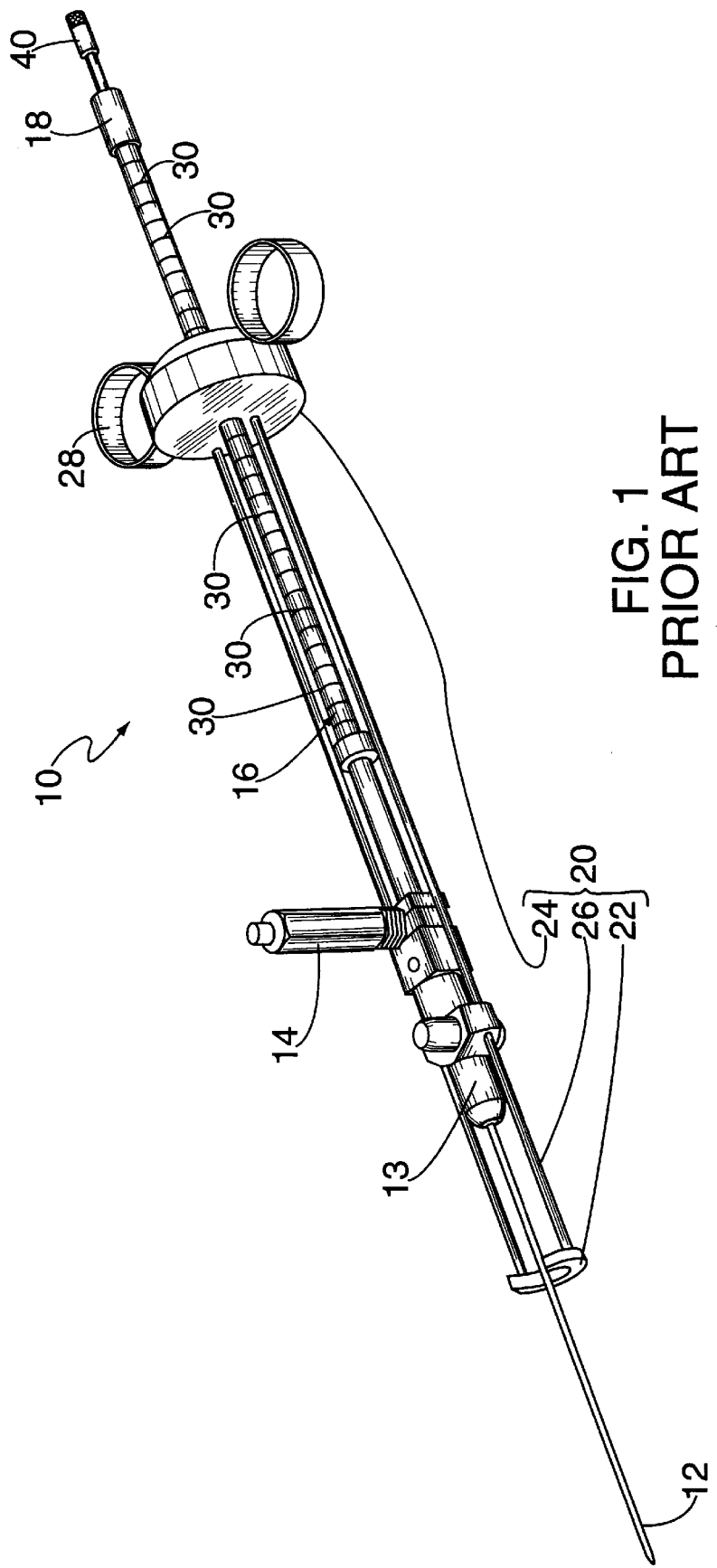
FIG. 1 is a perspective view of a seed applicator in accordance with the prior art.

Like reference characters denote like parts in the drawings.

FIG. 1 illustrates an applicator 10 in accordance with the prior art. The applicator 10 includes a hollow needle 12 insertable into the patient's body, a needle chuck 13 for releasably holding the needle, a magazine 14 for holding and dispensing seeds into the needle chuck 13, a main barrel 16 connected to the chuck 13, and a stylet 18 extendable through the main barrel 16, chuck 13, and needle 12 bores. The applicator 10 also includes a base frame member 20 along which the needle 12, needle chuck 13, magazine 14 and main barrel 16 are slidably mounted. The frame member 20 includes an abutment end 22 adapted to abut a surface of the patient's body or a template (not shown) fixed with respect to the body, a barrel collar 24 through which the main barrel 16 is slidable, and two rods 26 extending between and fixedly attached to the abutment end 22 and the collar 24. A pair of finger rings 28 for receiving a user's fingers are mounted on the collar 24.

The applicator 10 is designed to allow the needle 12 to be incrementally moved with respect to the base frame 20. For this purpose, the main barrel 16 includes a plurality of annular notches or indentations 30 that are equally spaced along the length of the barrel 16. A spring-loaded ball plunger (not shown) mounted in the barrel collar 24 is successively seated in each indentation 30 as the main barrel 16 is moved through the collar 24. As the plunger engages each indentation 30, the barrel 16 is releasably fixed in the collar 24, and the user is provided with a tactile and/or audible indication of the distance moved by the barrel 16. Accordingly, the needle 12, which moves with the barrel 16, can be retracted from the patient's body in a series of discrete distances equal to the distances separating the annular indentations 30 on the barrel 16.

Figure 2:
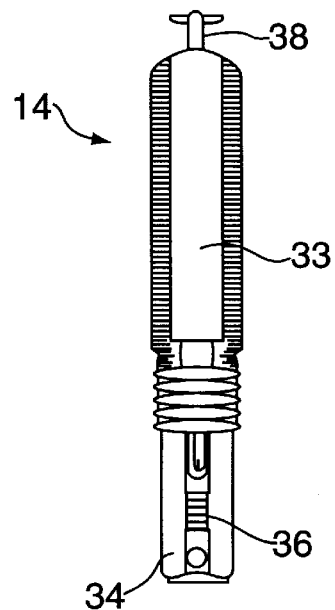
FIG. 2 is an enlarged side elevation view of the magazine of the FIG. 1 seed applicator.

The magazine 14, which is shown in greater detail in FIG. 2, includes a magazine head 33 and a seed cartridge 34 in which seeds 36 are stacked parallel to each other. A spring-loaded magazine plunger 38 is biased against the seeds 36 at the upper end of the magazine 14 to facilitate seed movement into the needle chuck 13 and to provide an indication to the operator that seed has been dispensed from the cartridge 34.

The stylet 18, which is extendable through the bores of the main barrel 16, the needle chuck 13, and the needle 12, includes a stylet handle 40 at its distal end. The handle 40 can be held by an operator to control movement of the stylet 18 during use (as shown in FIG. 4).

Figure 3:
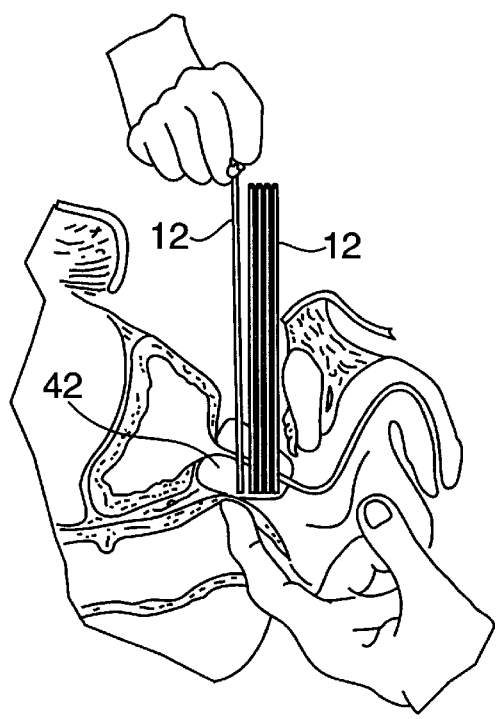
FIG. 3 is a schematic view illustrating insertion of hypodermic needles in a patient's prostate gland as an initial step in the operation of the FIG. 1 applicator.
Figure 4:
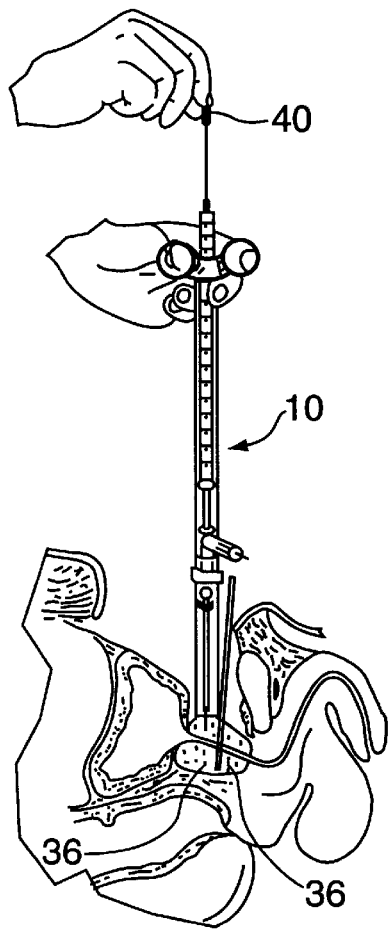
FIG. 4 is a schematic view illustrating operation of the FIG. 1 seed applicator for implanting seeds in the prostate gland.

Operation of the prior art applicator 10 for implanting seeds 36 in a patient's prostate gland 42 is illustrated in FIGS. 3 and 4. First, a plurality of needles 12 are inserted into the patient's prostate gland 42 in areas 15 where rows of seeds are to be implanted as shown in FIG. 3. A template (not shown) may be used to facilitate positioning of the needles 12. Then, the needle chuck 13 of the body of the applicator 10 is coupled with the protruding end of one of the needles 12 to prepare the applicator for use as shown in FIG. 4. The stylet 18, which is initially fully extended in the needle 12, is retracted from the needle 12 and the needle chuck 13, causing a seed 36 from the magazine 14 to be transferred in the chuck for movement into the needle 12. The stylet 18 is then pushed through the barrel 16 and the chuck 13 against the seed 36, advancing the seed 36 through the needle 12 and into the prostate gland 42. When the stylet is retracted, another seed is moved into the chuck. At the same time, the extended magazine plunger 38 will move further into the magazine 14, which movement will indicate to the operator that a seed 36 has been positioned in the chuck for transfer into the needle 12.

After a first seed 36 has been implanted, the needle 12 is partly retracted from the patient's body so that the next seed implanted is spaced apart from the first seed. The needle 12 is withdrawn by retracting the main barrel 16 through the barrel collar 24 until the ball plunger in the collar 24 engages the next indentation 30 in the barrel 16. As previously noted, this provides the operator with a tactile and/or audible indication that the needle is in position for another seed implant. Then, the stylet 18 is again retracted to enable the next seed 36 from the magazine 14 to be positioned for movement into the needle 12. The stylet 18 is then advanced through the needle 12 to force the next seed 36 into the patient's body at a distance away from the first seed corresponding to the distance between the barrel indentations 30. This procedure is repeated for subsequent seed implants.

While the prior art applicator 10 allows seeds to be quickly and accurately placed at equally spaced apart locations, it is not easily useable to place the seeds in varied spacing arrangements, which in some cases are clinically advantageous.

FIGS. 5 and 6 illustrate an applicator 100 in accordance with the present invention. The applicator 100 can be used easily, quickly, and accurately to vary the spacing of seeds implanted in a patient's body. The applicator 100 comprises a hollow needle 12 insertable into the patient's body, a needle chuck 113 for releasably holding the needle, a magazine 114 for holding and dispensing seeds into the needle chuck 113, a main barrel 116 connected to the needle chuck 113, and a stylet 117 extendable through the main barrel 116, needle chuck 113, and needle 12 bores. As with the prior art applicator 10, the applicator 100 also includes a base frame member 120 along which the needle 12, needle chuck 113, magazine 114 and main barrel 116 are slidably mounted. The frame member 120 includes an abutment end 22 adapted to abut a surface of the patient's body or a template (not shown) fixed with respect to the body, a barrel collar 124 through which the main barrel 116 is slidable, and two rods 26 extending between and fixedly attached to the abutment end 22 and the collar 124. The collar 124 is equipped with a finger ring 128 for receiving a finger of the user.

The applicator 100 is designed to allow the needle 12 to be moved in different increments with respect to the base frame 120. For this purpose, the main barrel 116 includes five rows or series of equally spaced ball detents or indentations 52, which rows extend along the length of the barrel 116. (One row 50 is shown in FIG. 5 and another row 51 is shown in FIG. 6.) Each row has different indentation spacing. For example, the applicator 100 has a first row of indentations spaced at 3.75 mm, a second row of indentations spaced at 4.0 mm, a third row of indentations spaced at 5.0 mm, a fourth row of indentations spaced at 5.5 mm, and a fifth row of indentations at 6.0 mm. These spacings can be changed as desired by using an applicator having a main barrel with other indentation spacings.

As shown in FIG. 7, the barrel collar 124 includes a fixed portion 55 and a spacing dial 56 rotatably mounted on the fixed portion 55. An operator can turn the dial 56 relative to the fixed portion 55 to select one of the five rows or series of indentations. A spring-loaded ball plunger 58 housed in the fixed portion 55 can be seated in one of five ball detents 60 (one shown in FIG. 7) located in an indexer bushing 62 that is fixed to the spacing dial and rotatably mounted on the main barrel. The five ball detent positions 60 in the collar are indexed to the five rows of indentations in the main barrel 116. The spacing dial 56 is equipped with a pointer 64 that rotates with the spacing dial 56 to indicate the row spacing selected.

A spring-loaded ball plunger 54 housed in the spacing dial 56 is successively seated in each indentation of a selected row thereby acting as an audible and/or tactile spacing indicator as the main barrel 116 is retracted through the barrel collar 124.

As the plunger 54 successively engages each indentation 52 of a selected row, the barrel 116 is momentarily fixed in the collar 124, and the user is provided with a tactile and/or audible indication of the distance moved by the barrel 116. Accordingly, the needle 12, which moves with the barrel 116, can be retracted from the patient's body in a series of discrete distances equal to the distances separating the annular indentations 130 of a selected row on the barrel 116.

The magazine 114 includes a magazine head 133 and a seed cartridge 134 in which seeds 36 are stacked parallel to each other. A spring-loaded magazine plunger 38 is biased against the seeds 36 at the upper end of the magazine 114 to facilitate seed movement into the needle chuck 113 and to provide an indication to the operator that seed has been dispensed from the cartridge 134.

Figure 8:
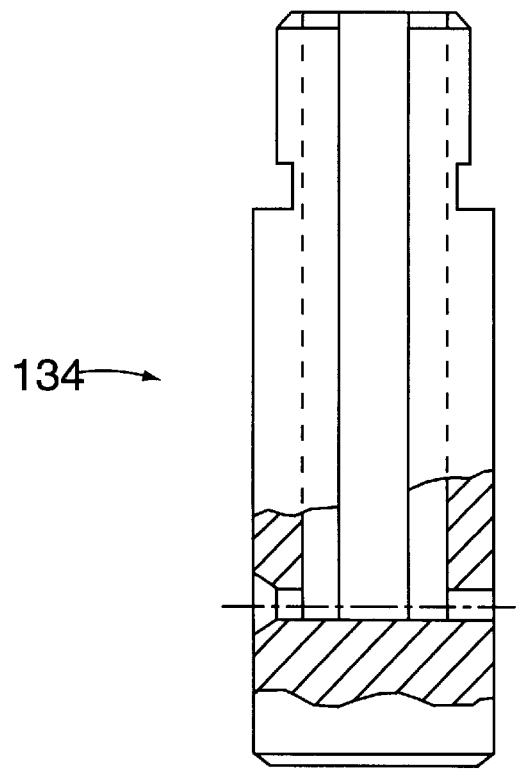
FIG. 8 is an enlarged right side elevation view of the seed cartridge of the magazine of the FIG. 5 applicator.
Figure 9:
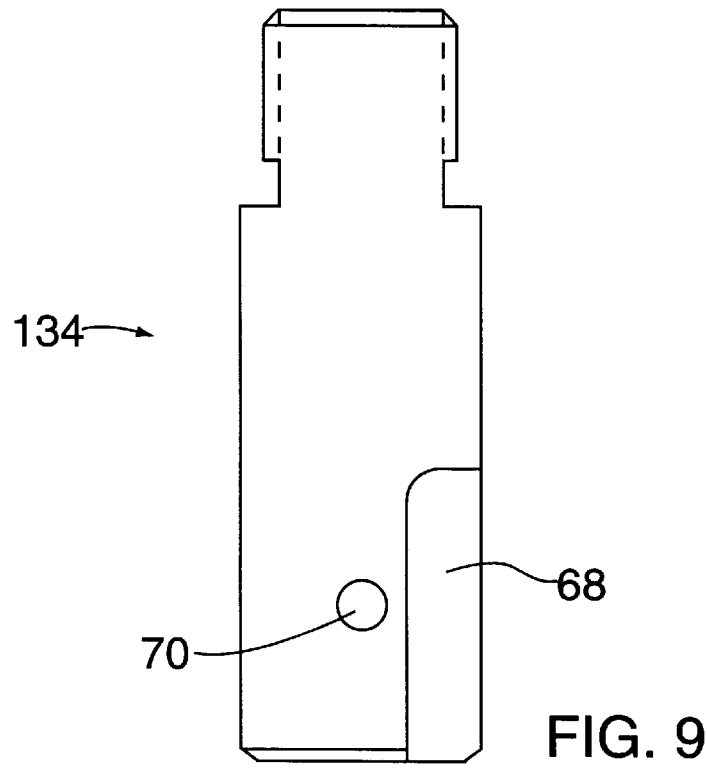
FIG. 9 is an enlarged left side, partially sectioned view of the FIG. 10 seed cartridge.

The seed cartridge 134, which is shown separately in FIGS. 8 and 9, is injection molded and disposable. The cartridge 134 can be preloaded with up to 15 seeds and then screwed into the magazine head 133.

The cartridge 134 is keyed to the needle chuck 113 to prevent its incorrect insertion into the needle chuck 113.

Specifically, the needle chuck 113 includes an orientation pin 66 (the rear side of which is shown in FIG. 5) extending into a hole in which the magazine is retained. As shown in FIG. 9, the left side of the cartridge 134 includes a recess or notch 68 to mate with the orientation pin 66 when the cartridge 134 is correctly oriented in the chuck 113. The orientation pin/recess mechanism prevents insertion of the cartridge 134 in any other orientation.

As shown in FIG. 9, the left side of the cartridge 134 also includes a ball detent 70, in which a ball plunger 72 in the chuck 113 is seated when the magazine 114 is inserted in the chuck 113 to releasably secure the magazine 114 therein. A properly inserted magazine 114 will therefore be securely retained in the chuck 113 during use of the applicator 100.

The stylet 117, which is extendable through the bores of the main barrel 116, the needle chuck 113, and the needle 12, includes a ball-shaped stylet handle 135 at its distal end. The handle 135 can be held by an operator to control movement of the stylet 117 during use of the applicator 100.

As with the prior art applicator 10, in the operation of the applicator 100 for prostate gland treatment, a plurality of needles 12 are first inserted into the patient's prostate gland 42 in areas where rows of seeds are to be implanted as shown in FIG. 3. A template (not shown) may be used to facilitate positioning of the needles 12. Then, the needle chuck 113 of the body of the applicator 100 is coupled with the protruding end of one of the needles 12 to prepare the applicator 100 for use. In accordance with the present invention, the initial seed spacing is set by adjusting the spacing dial 56 to select a particular row of indentations 52 on the main barrel 116 corresponding to the desired spacing. The stylet 117, which is initially fully extended in the needle 12, is then retracted from the needle 12 and the needle chuck 113, enabling a seed 36 from the magazine 114 to be positioned in the chuck 113 for movement into the needle 12. As a seed is moved into the chuck when the stylet is retracted, the extended magazine plunger 38 will move further into the magazine 114, which will indicate to the operator that a seed 36 has been positioned for transfer into the needle 12. The stylet 117 is then pushed through the barrel 116 against the seed 36, forcing the seed 36 through the needle 12 and into the patient's body.

After a first seed 36 has been implanted, the needle 12 is withdrawn from the patient's body by a particular distance so that the next seed implanted is spaced apart from the first seed. The needle 12 is then withdrawn by retracting the main barrel 116 through the barrel collar 124 until the ball plunger 54 in the collar 124 engages the next indentation 52 of the row selected in the barrel 116. As previously noted, this provides the operator with a tactile and/or audible indication that the needle is in position for another seed implant. Then, the stylet 117 is again retracted to enable the next seed 36 from the magazine 114 to be positioned for movement into the needle 12. The stylet 117 is then advanced through the needle 12 to force the seed 36 into the patient's body at a distance away from the first seed corresponding to the distance between the barrel indentations 52. This procedure is repeated for subsequent seed implants. After any seed has been implanted, the seed spacing can be changed by turning the spacing dial 56 such that the spacing of another row of indentations is selected. In this manner, the operator can easily and accurately vary seed spacing as desired.

While the present invention is described with reference to specific embodiments, it will be apparent to persons skilled in the art that many modifications and variations are possible. Accordingly, the present invention embraces all alternatives, modifications and variations that fall within the spirit and scope of the appended claims and all equivalents thereof.

We claim:

1. An applicator for implanting seeds at spaced locations in a patient's body, comprising:

a base member adapted to be positioned, during use of the applicator, generally stationary with respect to a surface of the patient's body;

a needle slidably mounted with respect to the base member and insertable into the patient's body, the needle including a bore extending therethrough;

a seed magazine for dispensing seeds into the bore of the needle;

a stylet extendable through the needle bore adapted to force seeds in the bore into the patient's body; and adjusting means comprising first means for releasably fixing the needle in a first set of positions relative to the base member and second means for releasable fixing the member, wherein the first set of positions are generally equally spaced from one another by a first distance and the second set of positions are generally equally spaced by a second distance, the second distance being different from the first distance, in order to enable seeds to be implanted at variably spaced locations in the patient's body, wherein the first and second means are spaced laterally from one another.

2. The applicator of claim 1, further comprising a needle chuck for releasably coupling the needle, wherein the magazine is releasably mounted on the chuck.

3. The applicator of claim 2, wherein the magazine is mountable on the chuck in only one orientation of the magazine relative to the chuck.

4. The applicator of claim 3, wherein the chuck includes an index pin and the magazine includes a recess for receiving the index pin to orient the magazine in the one orientation.

5. The applicator of claim 1, wherein said magazine includes a magazine plunger biased in a direction toward the bore of the needle.

6. An applicator for implanting seeds at spaced locations in a patient's body, comprising:

a base member adapted to be positioned, during use of the applicator, generally stationary with respect to a surface of the patient's body;

a needle slidably mounted with respect to the base member and insertable into the patient's body, the needle including a bore extending therethrough;

a seed magazine for dispensing seeds into the bore of the needle;

a stylet extendable through the needle bore adapted to force seeds in the bore into the patient's body; and adjusting means for releasably fixing the needle in at least two sets of variably spaced positions relative to the base member in order to enable seeds to be implanted at variably spaced locations in the patient's body, wherein the adjusting means comprise a barrel attached to the needle, the barrel including at least two series of spaced indentations, the indentations in one series being generally equally spaced by a first distance and the indentations in another series being generally equally spaced by a second distance different than the first distance, the adjusting means also comprising a ball plunger movably mounted in the base member, the ball plunger being successively engageable with the indentations as the barrel is moved with respect to the base member to releasably fix the needle relative to the base member in the variably spaced positions.

7. The applicator of claim 6, further comprising a spacing dial for selecting one of the series of indentations to be engaged by the ball plunger.

8. The applicator of claim 7, wherein the base member includes a dial ball plunger engageable with one of a plurality of detents in an indexer bushing affixed to the spacing dial, each the detents being indexed to one of the series.

9. The applicator of claim 7, wherein the spacing dial includes a pointer to indicate the series selected.

10. The applicator of claim 6, wherein the barrel includes a first, second, third, fourth, and fifth series of indentations having indentation spacings of 3.75 mm, 4 mm, 5 mm, 5.5 mm and 6 mm, respectively.

11. The applicator of claim 6, wherein said base member further comprises a collar through which said barrel is slidable, an abutment end adapted to abut a surface of the patient's body or an object generally stationary with respect to the body, and a rod extending between and fixedly connected to said abutment end and said collar.

* * * * *